US009297955B2

(12) United States Patent
Bartoli et al.

(10) Patent No.: US 9,297,955 B2
(45) Date of Patent: Mar. 29, 2016

(54) PLASMONIC INTERFEROMETER SENSOR

(75) Inventors: Filbert Bartoli, Center Valley, PA (US); Qiaoqiang Gan, East Amherst, NY (US); Yongkang Gao, Bethlehem, PA (US)

(73) Assignee: LEHIGH UNIVERSITY

( * ) Notice: Subject to any disclaimer, the term of this patent is extended or adjusted under 35 U.S.C. 154(b) by 0 days.

(21) Appl. No.: 14/343,906

(22) PCT Filed: Sep. 6, 2012

(86) PCT No.: PCT/US2012/053882
§ 371 (c)(1),
(2), (4) Date: Mar. 10, 2014

(87) PCT Pub. No.: WO2013/112201
PCT Pub. Date: Aug. 1, 2013

(65) Prior Publication Data
US 2014/0218738 A1 Aug. 7, 2014

Related U.S. Application Data

(63) Continuation-in-part of application No. 12/894,699, filed on Sep. 30, 2010, now Pat. No. 8,649,014.

(60) Provisional application No. 61/532,791, filed on Sep. 9, 2011, provisional application No. 61/248,114, filed on Oct. 2, 2009.

(51) Int. Cl.
*G01N 21/01* (2006.01)
*G02B 6/122* (2006.01)
(Continued)

(52) U.S. Cl.
CPC ............... *G02B 6/1226* (2013.01); *B82Y 20/00* (2013.01); *G01N 21/01* (2013.01); *G01N 21/45* (2013.01); *G01N 21/7703* (2013.01); *G01N 21/553* (2013.01); *G01N 2021/5903* (2013.01); *G01N 2021/7779* (2013.01)

(58) Field of Classification Search
CPC ...... G02B 6/1226; G02B 5/008; G02B 27/52; B82Y 20/00; G01N 21/4133; G01N 2021/779; G01N 21/553; G01N 21/554
USPC .......................................... 356/445
See application file for complete search history.

(56) References Cited

U.S. PATENT DOCUMENTS

2006/0291780 A1* 12/2006 Sato et al. ........................ 385/39
2007/0262405 A1* 11/2007 Furuyama ..................... 257/432
(Continued)

OTHER PUBLICATIONS

Wang et al., "The Transmission Characteristics of Surface Plasmon Polaritons in Ring Resonator." Optics Express, vol. 17, Issue 26, pp. 24096-24101. Dec. 17, 2009. US.
(Continued)

*Primary Examiner* — Michael P Lapage
(74) *Attorney, Agent, or Firm* — The Belles Group, P.C.

(57) ABSTRACT

An optical device includes a transparent substrate and a conductive layer disposed over an upper surface of the transparent substrate. The conductive layer defines at least one groove inwardly extending from an upper surface and includes an aperture that is spaced apart from the at least one groove. An interface between the upper surface of the conductive layer and an ambient medium defines an optical branch along which surface plasmon polariton modes are excited in response to at least partially coherent light being received by the optical device.

8 Claims, 15 Drawing Sheets

(51) Int. Cl.
  *B82Y 20/00*   (2011.01)
  *G01N 21/77*   (2006.01)
  *G01N 21/45*   (2006.01)
  *G01N 21/59*    (2006.01)
  *G01N 21/552*   (2014.01)

(56) References Cited

U.S. PATENT DOCUMENTS

| | | | |
|---|---|---|---|
| 2008/0064035 A1* | 3/2008 | Densham | 435/6 |
| 2008/0129980 A1 | 6/2008 | Dhawan et al. | |
| 2008/0185521 A1 | 8/2008 | Hollingsworth | |
| 2009/0146081 A1* | 6/2009 | Stark | 250/492.2 |
| 2009/0251771 A1* | 10/2009 | Hendriks et al. | 359/342 |
| 2011/0051142 A1* | 3/2011 | Yanagisawa et al. | 356/445 |
| 2011/0063717 A1* | 3/2011 | Consonni et al. | 359/298 |
| 2011/0075254 A1* | 3/2011 | Cui et al. | 359/370 |
| 2011/0080589 A1 | 4/2011 | Gan et al. | |

OTHER PUBLICATIONS

Qiaoqiang et al., "Vertical Plasmonic Mach-Zehnder Interferometer for Sensitive Optical Sensing," IEEE Photonics Society, 23rd Annual Meeting, pp. 160-161. Nov. 11, 2010 US.

International Search Report for PCT/US2012/053882, Filed Sep. 6, 2012. WO.

* cited by examiner

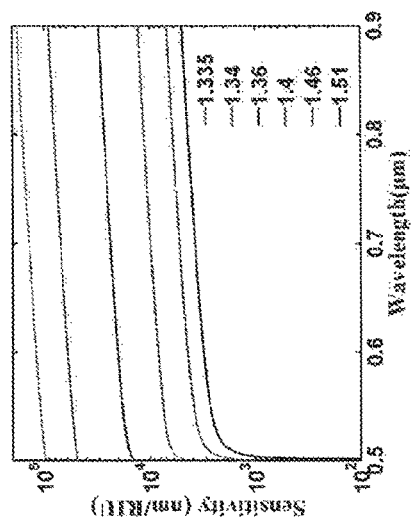
FIG. 3
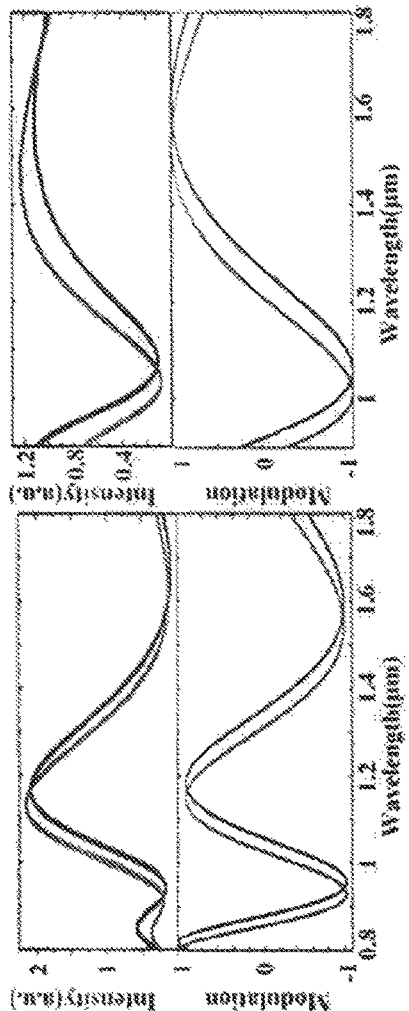
FIG. 4A
FIG. 4B
FIG. 4C

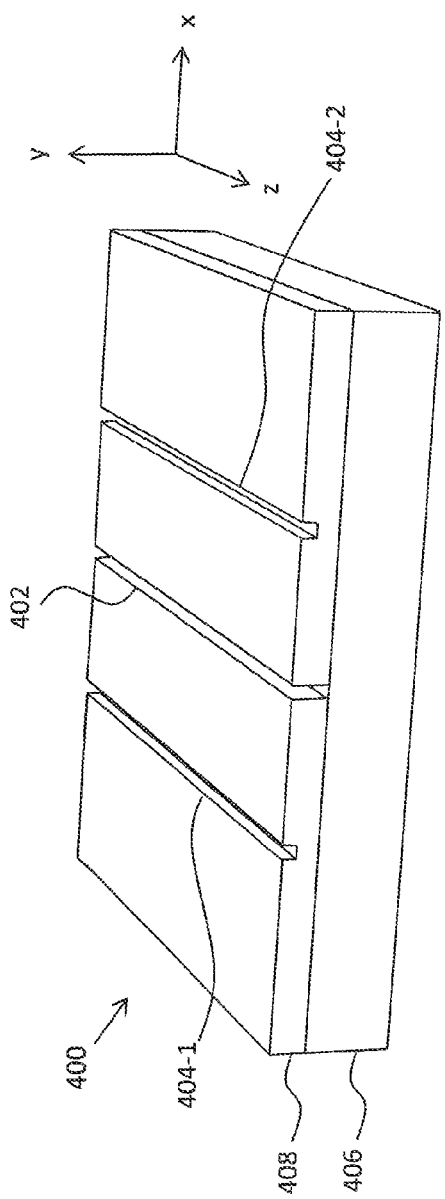
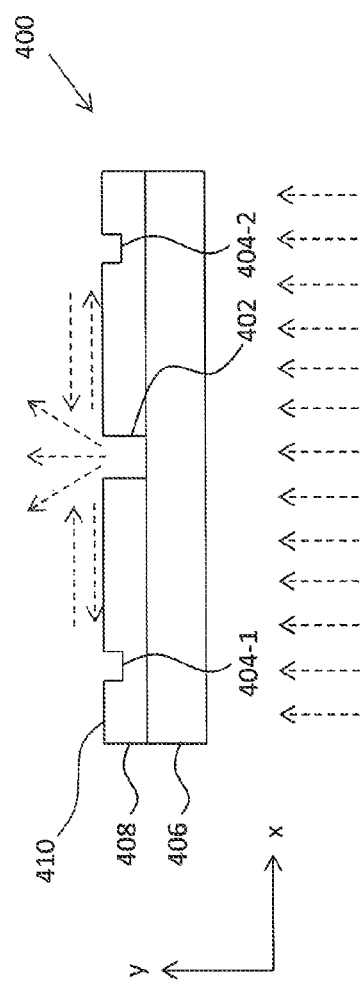
FIG. 13A
FIG. 13B

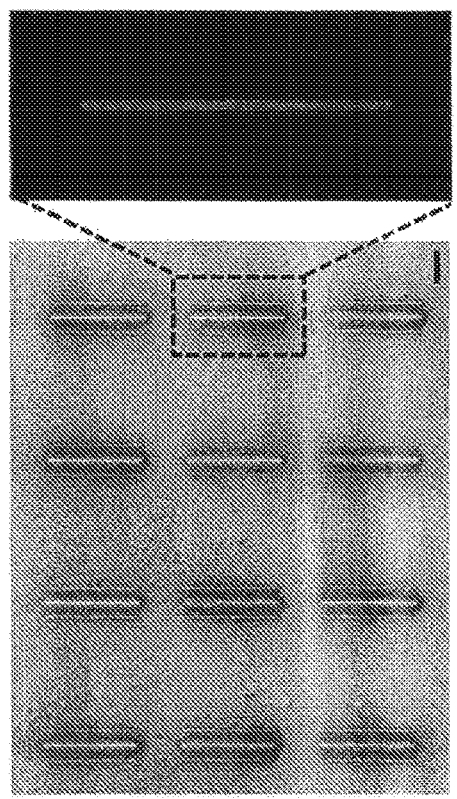
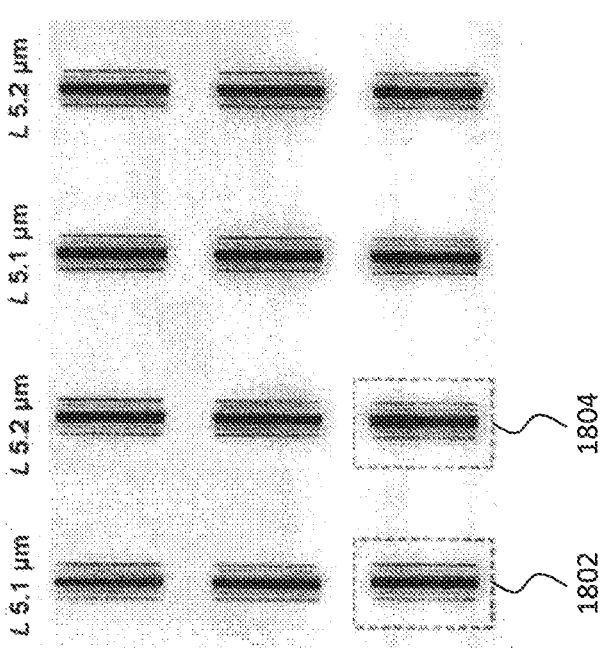
FIG. 18C
FIG. 18B
FIG. 18A

PLASMONIC INTERFEROMETER SENSOR

CROSS-REFERENCE TO RELATED APPLICATIONS

This application is a continuation-in-part of U.S. patent application Ser. No. 12/894,699, filed Sep. 30, 2010 claiming priority to U.S. Patent Application No. 61/248,114, filed on Oct. 2, 2009, and claims priority to U.S. Patent Application No. 61/532,791 filed Sep. 9, 2011, the entireties of which are herein incorporated by reference.

STATEMENT OF GOVERNMENTAL INTEREST

This invention was made with Government support from the National Science Foundation—Bioengineering & Environmental Systems under awards 0608742 and 1014957, the National Science Foundation—Electrical, Communications and Cyber Systems under awards 0901324 and 1128086, and from the Department of Defense—Army Research Laboratories, Army Optics V and VI. The Government may have certain rights in this invention.

FIELD OF DISCLOSURE

The disclosed system and method relate to interferometry. More specifically, the disclosed system and method relate to interferometry utilizing vertical and circular plasmonic interferometers.

BACKGROUND

Interferometry is one of the most sensitive optical interrogation methods and has been used in a wide array of technologies including astronomy, fiber optics, engineering metrology, quantum mechanics, plasma physics, remote sensing, and biomolecular interactions such as screening molecular interactions in surface binding modes. Several types of interferometry have been developed such as fluorescence interferometry for high resolution microscopy or nanoscopy, label-free sensing based on a Mach-Zehnder Interferometer, a Young Interferometer, a dual polarization interferometer, back-scattering interferometry, and spectral reflectance interferometry, to name a few.

Surface Plasmons ("SPs") are coherent oscillations of conduction electrons on a metal surface excited by electromagnetic radiation at a metal-dielectric interface. The sensitivity of the Surface Plasmon Resonance ("SPR") to the refractive index change at a flat metal interface has led to the development of SPR sensing systems based on interferometry and that use prisms to couple light into a single surface-plasmon mode on a flat, continuous metal film (e.g., gold). However, the relatively large size of these experimental systems is a disadvantage for applications requiring integrated, low-cost, compact, image-based devices for portable, rapid bio-analytical measurements.

Nanoplasmonic biosensors, employing nanoscale metal particles, provide an attractive miniaturized platform for sensitive, label-free monitoring of cellular processes. When receptor molecules are immobilized on the nanostructured metal surface, the binding of target biomolecules changes the local refractive index, which affects the optical properties of the SP modes and permits optical detection. Recent advances in nanofabrication, nanomaterial synthesis, and nanocharacterization permit significant advances over conventional SPR evanescent wave-based biosensors, whose large size limits their effectiveness for probing nanovolumes and single cells, and for integration into microfluidic platforms. However, the sensitivities for these nanoplasmonic structures are much lower (two to three orders of magnitude) than other sensitive optical sensing technologies.

SUMMARY

An optical device is disclosed that includes a transparent substrate and a conductive layer disposed over an upper surface of the transparent substrate. The conductive layer defines at least one groove inwardly extending from an upper surface and an aperture that is spaced apart from the at least one groove. An interface between the upper surface of the conductive layer and an ambient medium defines an optical branch along which surface plasmon polariton modes are excited in response to at least partially coherent light being received by the optical device.

In some embodiments, a vertical plasmonic interferometer includes a substrate and a conductive layer. The substrate includes first and second opposed surfaces and is configured to transmit light received at the first surface to the second surface and to transmit light received at the second surface to the first surface. The conductive layer includes a third surface that is disposed on an opposite side of the conductive layer than a fourth surface. The fourth surface defines an interface with an ambient medium. The conductive layer defines at least one groove inwardly extending from the fourth surface and defines an aperture that is spaced apart from the at least one groove. The interface between the fourth surface and the ambient medium defines an optical branch along which surface plasmon polariton modes are excited in response to at least partially coherent light being received by the vertical plasmonic interferometer.

BRIEF DESCRIPTION OF THE DRAWINGS

FIG. 3 illustrates a sensitivity versus wavelength graph demonstrating the theoretical sensitivity of a vertical plasmonic Mach-Zehnder interferometer in accordance with FIG. 1.

FIGS. 4A-4C illustrate numerical modeling for an interference signal of the scattered light from a slit in Au film in accordance with the vertical plasmonic Mach-Zehnder interferometer illustrated in FIG. 1 for various refractive indices.

FIG. 13A is an isometric view of another example of a plasmonic interferometer.

FIG. 13B is a cross-sectional view of the plasmonic interferometer illustrated in FIG. 13A.

FIG. 18A is a bright-field microscope image of an array of fabricated plasmonic interferometers in accordance with FIGS. 13A-13C.

FIG. 18B is a scanning electron microscope image of the plasmonic interferometer array illustrated in FIG. 18A.

FIG. 18C is a CCD image of one of the plasmonic interferometers of the array illustrated in FIGS. 18A and 18B.

DETAILED DESCRIPTION

Figure 1:
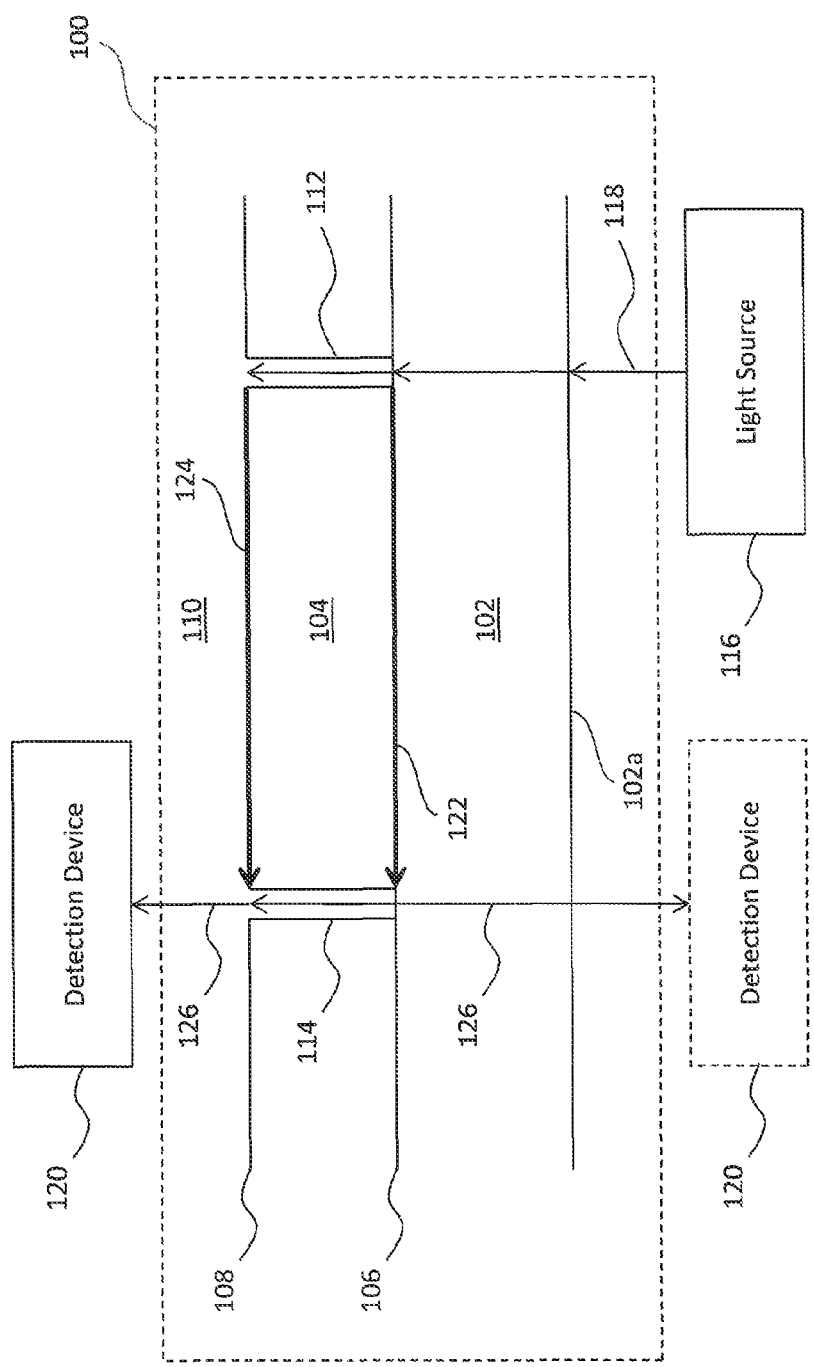
FIG. 1 illustrates one example of a vertical plasmonic Mach-Zehnder interferometer.

This description is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Various vertical plasmonic interferometers are disclosed. In some embodiments, a vertical plasmonic Mach-Zehnder interferometer ("VPMZI") is disclosed that provides high sensitivity optical sensing. The VPMZI enables optical microscopes to perform Surface Plasmon Resonance ("SPR") sensing thereby eliminating the need for the conventional bulky and expensive angular tunable systems. The flexibility provided by the VPMZIs advantageously enables future microscopes to integrate SPR sensing functionality, which should have significant commercial potential. Additionally, the compact package of the VPMZIs disclosed herein may be integrated into sensitive biosensing platforms and subwavelength optics on a chip.

The VPMZI 100 illustrated in FIG. 1 includes a first substrate 102 on which a second substrate 104 is disposed. A first interface 106 is defined between substrate 102 and substrate 104, and a second interface 108 is defined by substrate 104 and ambient medium 110. Second substrate 104 defines first and second slits 112, 114, which are horizontally spaced apart from one another. A light source 116 may be configured to direct light 118 towards first slit 112, and a detection device 120 may be configured to receive scattered light 126 from second slit 114.

Substrate 102 is fabricated from glass and may have a variety of thicknesses and widths. Examples of substrate 102 include, but are not limited to, glass, Quartz, and other transparent semiconductor substrates.

Substrate 104 is a metal-containing layer having a thickness approximately on the order of tens or hundreds of nanometers depending on the material from which substrate 104 is fabricated. Such materials include, but are not limited to, gold, silver, copper, and aluminum, to name only a few possible materials. Substrate 104 may be deposited on substrate 102 in a variety of methods including, but not limited to, chemical vapor deposition ("CVD"), atomic layer deposition ("ALD"), electroless plating, and sputtering and evaporation.

Slits 112 and 114 may be formed in substrate 104 by utilizing a wide variety of methods, such as focused ion beam ("FIB") milling, electron beam ("e-beam") lithography, and nano-imprint lithography. The thicknesses of slits 112 and 114 are on the order of one to several hundreds of nanometers and may vary depending on the material used for substrate 104 in order to couple visible and near visible infrared light. For example, if substrate 104 is a 200 nm-thick silver film deposited on a glass substrate and includes two parallel slits 112 and 114 that are separated from each other by approximately 97 μm, then slits 112 and 114 may be approximately 100 nm wide and 40 μm long for use with wavelengths between 800 and 900 nm. Slits 112 and 114 may also be disposed from one another at various distances on the order of several microns to tens of microns and beyond.

Interface 106 between substrate 102 and substrate 104 defines a first optical branch or optical transmission path capable of supporting at least one surface plasmon polariton ("SPP") mode. Similarly, interface 108 between substrate 104 and ambient medium 110 defines a second optical branch capable of supporting at least one SPP mode having a different phase than the SPP mode of interface 106. Medium 110 may be a dielectric material in the form of a solid, liquid, or gas. In some embodiments in which VPMZI 100 is integrated into a biologic sensing device, medium 110 is a liquid, such as water, that includes a sample of biologic material to be tested, and in some embodiments, medium 110 is air. However, one skilled in the art will understand that VPMZI 100 may be disposed within a variety of different mediums for testing.

Light source 116 may be any light source that provides light 118 that is at least partially coherent. For example, light source 116 may be a halogen lamp, light emitting diode ("LED"), or a laser, to name a few possible partially coherent light sources. Light source 116 may be disposed adjacent to substrate 102 such that light 118 emitted by light source 116 contacts a surface 102a of substrate 102, which is on the opposite side of substrate 102 as interface 106. Light 118 may be emitted from light source 116 such that it is parallel to a plane defined by surface 102a of substrate 102 and is approximately aligned with an axis defined by slit 112 defined by substrate 104. In some embodiments, light source 116 emits light 118 at an angle other than a right angle with respect to a plane defined by surface 102a of substrate 102. Additionally, a polarizer (not shown) may be coupled to the light source 116 to polarize the at least partially coherent light 118 emitted by light source 116. For example, the polarizer may polarize light 118 such that light 118 is perpendicular to slits 112 and 114.

Detection device 120 may be any device configured to detect optical signals emitted from slit 114 either through ambient medium 110 (shown in FIG. 1 as solid rectangle) or through substrate 102 (shown in FIG. 1 as dotted rectangle). Examples of detection devices 120 include, but are not limited to, spectrometers, monochromators, charged coupled device ("CCD") or complimentary metal-oxide semiconductor ("CMOS") image sensors. In some embodiments, detection device 120 may be a spectrum analyzer configured to receive and perform spectral analysis on the optical signals emitted from slit 114.

In operation, light source 116 emits at least partially coherent light 118 towards surface 102a of substrate 102. As described above, light 118 may be transmitted by light source 116 such that light 118 is emitted at an angle that is orthogonal to a plane defined by surface 102a, or light 118 may be transmitted by light source 116 at an angle other than ninety degrees with respect to a plane defined by surface 102a. Regardless of the angle at which light 118 is emitted with respect to the plane defined by surface 102a, light 118 is directed towards one of the slits 112, 114 defined by substrate 104.

The light 118 received at surface 102a of substrate 102 is transmitted through substrate 102 to interfaces 106 and 108 of substrate 102 at or near a location of one of the slits 112, 114 (in this example at slit 112). One or more SPP modes 122 and 124 are excited in each of the optical transmission paths defined by interfaces 106 and 108 in response to receiving light 118 from light source 116. SPP modes 122 and 124 propagate towards slit 114 where they constructively and destructively interfere with one another.

The interference of SPP modes 122 and 124 at slit 114 results in scattered light 126 being emitted from slit 114 toward ambient medium 110 and back into substrate 102. Detection device 120 may be positioned adjacent to substrate 104 or substrate 102 such that it receives scattered light 126. The interference pattern of the far-field scattering of SPP modes 122 and 124 includes the following term:

$$\cos\left[\frac{2\pi L}{\lambda}\left(\sqrt{\frac{e'_m(\lambda)n_{110}^2}{e'_m(\lambda)+n_{110}^2}} - \sqrt{\frac{e'_m(\lambda)n_{102}^2}{e'_m(\lambda)+n_{102}^2}}\right)\right] \qquad \text{Eq. (1)}$$

Where, $\in'_m$ is the real part of the permittivity of substrate 104;

$n_{110}$ is the refractive index of the ambient dielectric medium 110 adjacent to substrate 104;

$n_{102}$ is the refractive index of substrate 102;

L is the slit separation distance, i.e., the distance between slits 112 and 114;

λ is the wavelength of the partially coherent light; and $$\sqrt{\frac{e'_m(\lambda)n^2}{e'_m(\lambda)+n^2}}$$

is the effective refractive index ("ERI") of interface 108 between substrate 104 and ambient medium 110.

Notably, the two optical branches defined by interfaces 106 and 108 of VPMZI 100 may be separated by a gap that is only several hundred nanometers wide (i.e., the thickness of substrate 104 may be on the order of hundreds of nanometers), which is appreciably smaller than for silicon-based planar MZIs.

The phase modulation properties of VPMZI 100 are sensitive to changes in the refractive index in the sensing transmission path 108 relative to the refractive index in the reference transmission path 106. When the refractive index of the sensing transmission path 108, which is determined by the refractive index of ambient medium 110, $n_{110}$, is changed to $n_{110}+\Delta n_{110}$, the phase change is given by the following equation:

$$\Delta\varphi = \frac{2\pi L}{\lambda}\left(\sqrt{\frac{e'_m(\lambda)n_{110}^2}{e'_m(\lambda)+n_{110}^2}} - \sqrt{\frac{e'_m(\lambda)(n_{110}+\Delta n_{110})^2}{e'_m(\lambda)+(n_{110}+\Delta n_{110})^2}}\right) \qquad \text{Eq. (2)}$$

Figure 2A:
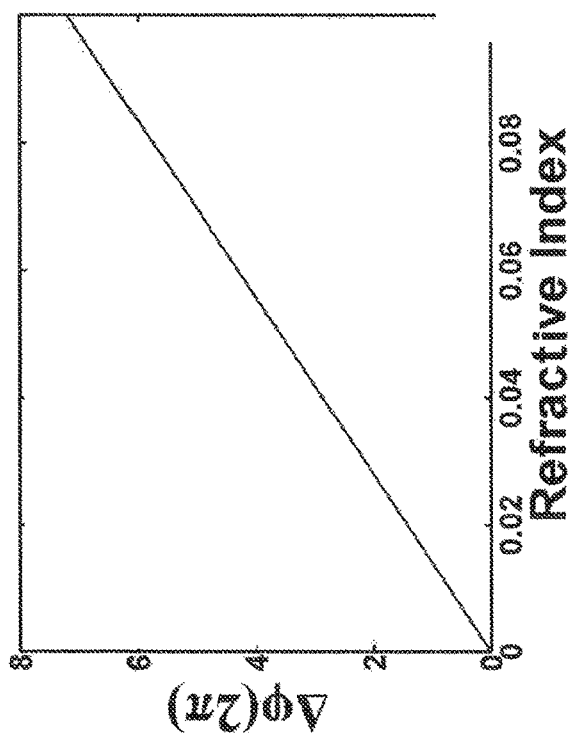
FIG. 2A illustrates the phase modulation properties of a vertical plasmonic Mach-Zehnder interferometer in accordance with FIG. 1.
Figure 2B:
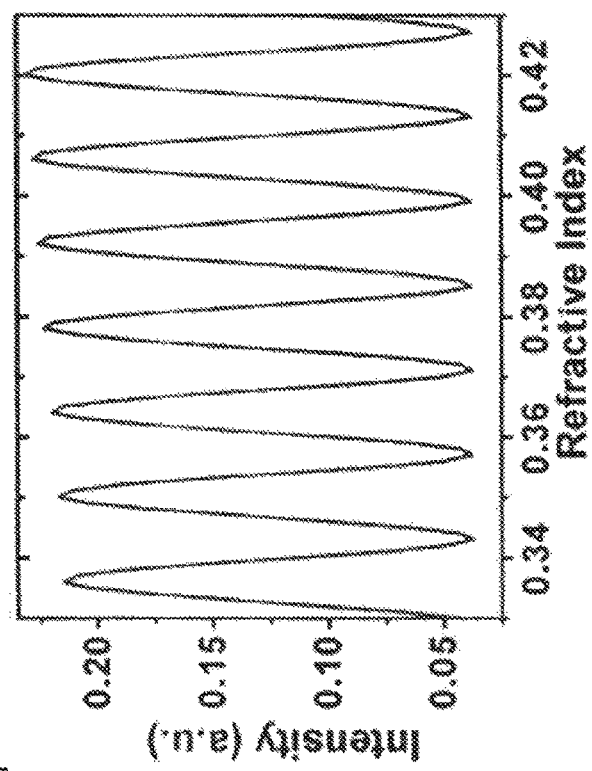
FIG. 2B illustrates a simulated intensity modulation of an output signal from a vertical plasmonic Mach-Zehnder in accordance with FIG. 1.

Equation 2 can be used to analyze the relation between the phase change and the refractive index change. In this calculation, an incident wavelength of 1033 nm is employed, for which the permittivity of silver (−48.81+i3.16) is used as substrate 104. Assuming that the ambient medium 110 is water ($n_{110}$=1.33) and the distance between slits 112 and 114, a refractive index change of 0.1 may introduce a phase change of about 7.2(2π:) as shown in FIG. 2A, which is in a good agreement with the two-dimensional ("2D") finite-difference-time-domain ("FDTD") modeling result shown in FIG. 2B. Based on the FDTD modeling result, more than seven periods of interference pattern can be observed in the far-field scattering signal, which can be utilized in optical sensing applications. The length of the sensing transmission path 108 is kept relatively short to minimize the intrinsic loss of metals. For example, transmission paths 106 and 108 may be on the order of tens of microns to hundreds of microns, although one skilled in the art will understand that transmission paths 106 and 108 may have other lengths. Consequently, the phase-change sensitivity of this metallic VPMZI (approximately 72(2π:)/refractive index unit ("RIU")) is much lower than Si-based MZIs with long sensing arms. For example, the phase-change sensitivity of a Si-based MZI with a 5 mm sensing arm is reported to be about 1400(2π)/RIU.

The double-slit or slit-groove metal VPMZI device 100 can also support spectral interference when the input is a broad band light source. Spectral interference is supported by the proposed VPMZI, which provides an ultrahigh sensitivity that is significantly better than has been reported for other nanoplasmonic architectures. For example, when the refractive index or the ambient medium 110 is changed, the peaks and valleys in the interference pattern will shift. The sensitivity may be derived by setting the right side of Equation 2 to a constant value, which yields the following equation:

$$S = \frac{\Delta\lambda}{\Delta n} = \frac{\lambda}{n'_m}\left(\frac{e'_m(\lambda)n_{110}^2}{e'_m(\lambda)+n_{110}^2}\right)^{3/2} / \left(\sqrt{\frac{e'_m(\lambda)n_{110}^2}{e'_m(\lambda)+n_{110}^2}} - \sqrt{\frac{e'_m(\lambda)n_{102}^2}{e'_m(\lambda)+n_{102}^2}}\right) \quad \text{Eq. (3)}$$

From Equation 3, it is seen that when $n_{110} < n_{102}$, the sensitivity value is negative, indicating that the interference pattern will shift to shorter wavelengths, whereas if $n_{110} > n_{102}$, then the sensitivity value is positive, indicating that the interference pattern will shift to longer wavelengths. Equation 3 also provides that the sensitivity increases if the two terms in the denominator are close in value. FIG. 3 illustrates the sensitivities that could potentially be achieved by varying the refractive index of the material of substrate 102. In this calculation, substrate 104 is gold and ambient medium 110 is water ($n_{110}$=1.33).

As an example, when $n_{102}$=1.51, the relation between the sensitivity and the operating wavelength is shown by the lowest curve in FIG. 3. The sensitivity cannot be enhanced by orders or magnitude by employing longer wavelengths. However, when the refractive index of substrate 102, $n_{102}$, is decreased and approaches that of ambient medium 110, $n_{110}$, the sensitivity can increase significantly as illustrated by the series of curves in FIG. 3.

Matching the ERI at of substrate 102 and ambient medium 110 increases the sensitivity of VPMZI 100. In one embodiment, the ERI matching condition is where the dispersion curve at the interface 108 is approximately equal to the dispersion curve at interface 106, which indicates that the ERI match condition could be met over a broad range of wavelengths. This can in principle be accomplished by providing a substrate 102 having a refractive index that is close to the refractive index of ambient medium 110. For example, fluorinated ethylene propylene copolymer (FEP) may be implemented as substrate 102 because it is chemically inert, thermoplastic, transparent in the visible region, and has a refractive index of 1.341 at the λ of 590 nm.

A 2D FDTD method was used to simulate the sensitivity for a gold substrate 108 disposed on substrates 102 having various refractive index values for a VPMZI 100 in accordance with FIG. 1 in which slits 112 and 114 were separated by approximately 70 μm and only slit 112 was illuminated by the incident light. The sensitivity from the shift in the peak or valley wavelength was calculated for a variety of different refractive indices. For example, if $n_{102}$=1.46, then when $n_{110}$ changes from 1.33 to 1.331, the peak of the interference pattern at 970 nm will shift to 964 nm, which indicates that the sensitivity is $-0.6 \times 10^4$ nm/RIU (see the upper panel in FIG. 4A). If $n_{110}$ is set to 1.36, then the valley of the interference pattern at 940 nm shifts to 908 nm, which indicates a sensitivity of about $-3.2 \times 10^4$ nm/RIU. Similarly, the peak at 1168 nm shifts to 1132 nm, which indicates a sensitivity of about $-3.6 \times 10^4$ nm/RIU as shown in the upper panel of FIG. 4B. Further decreasing $n_{110}$ to 1.35 provides a shift in the valley position from 1076 nm to 1034 nm, which indicates a sensitivity of $-4.2 \times 10^4$ nm/RIU. At the same time, the peak at 1582 nm shifts to 1486 nm, which indicates a sensitivity of about $-9.2 \times 10^4 \cdot$nm/RIU as shown in the upper panel of FIG. 4C. In accordance with the expression on the right side of Equation 2, the theoretical spectral interference pattern of this structure was calculated and plotted in the lower panels in FIGS. 4A-4C, which is in accordance with the FDTD modeling result. Remarkably, the sensitivities shown in FIGS. 4B and 4C are between one and two orders of magnitude larger than the best sensitivity previously reported for nanohole arrays (approximately 1500 nm/RIU).

If a low refractive index substrate is unavailable, then the ERI matching condition can also be met by various surface dispersion engineering approaches. For example, one can introduce a thin film of dielectric material with a higher refractive index on substrate 104 at interface 108 between substrate 104 and ambient medium 110 to tune the ERI of this interface. Various nanopatterned structures, such as periodic metal-dielectric-air grooves and surface grating structures can be employed to finely tune the shape of the dispersion curve and approach to the ERI match condition.

An experiment was performed to determine if spectral interference of light emitted from slot 114 is observable. The optical transmission measurements were performed on an IX81® inverted microscope available from Olympus America Inc. of Center Valley, Pa. using a white light beam 118 from a 100 W halogen lamp that was focused at nominal incidence onto surface 102a of substrate 102, which was a glass substrate, through the microscope condenser with a linear polarizer. The polarization of the incident light was transverse magnetic ("TM") with respect to the longitudinal axis of slit 112. The transmission light was collected by an 40× microscope objective with a numerical aperture of 0.6 coupled into a multimode fiber bundle connected with a fiber-based compact spectrometer, which was a USB4000 fiber optic spectrometer available from Ocean Optics, Inc. of Dunedin, Fla.

Figure 5:
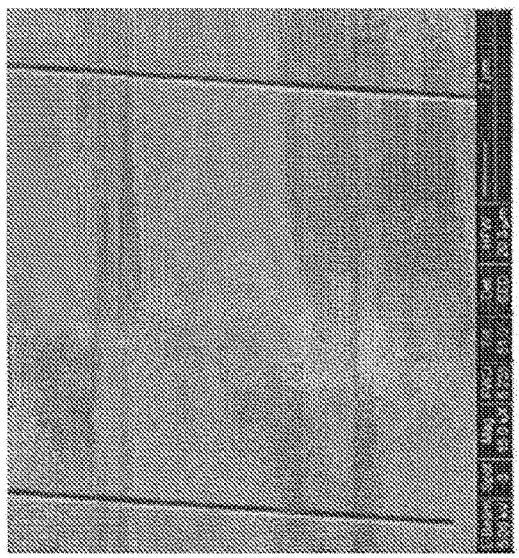
FIG. 5 is a scanning electron microscope image of a pair of slits formed on a metal substrate.

A charge coupled device ("CCD") camera was employed to align the position of the double slits. Consequently, the collection condition of the transmitted light from all the samples is almost identical. A diaphragm in the condenser was employed to minimize the intensity of the light beam illuminating the other slit 114. Several VPMZIs in accordance with FIG. 1 were fabricated using by creating slits 112 and 114 at various distances in 300 nm-thick layers of gold and silver (substrate 104) that were evaporated onto a flat fused silica microscope slide (substrate 102). Slits 112 and 114, which had a thickness of approximately 220 nm, were formed by FIB milling substrate 104 with a DualBeam™ 235 available from FEI Company of Hillsboro. Four samples on a silver film with slit-slit separation distances of 10.50, 13.12, 15.73 and 20.98 μm were observed and studied. A scanning electron microscope image of a VPMZI 100 having a slit-slit separation distance of 15.73 μm with slits 112 and 114 having widths of approximately 220 nm is shown in FIG. 5.

Further embodiments and experiments are described in the attachment entitled "Plasmonic Mach-Zehnder Interferometer for Ultrasensitive On-Chip Biosensing, which is incorporated herein in its entirety.

Figure 6:
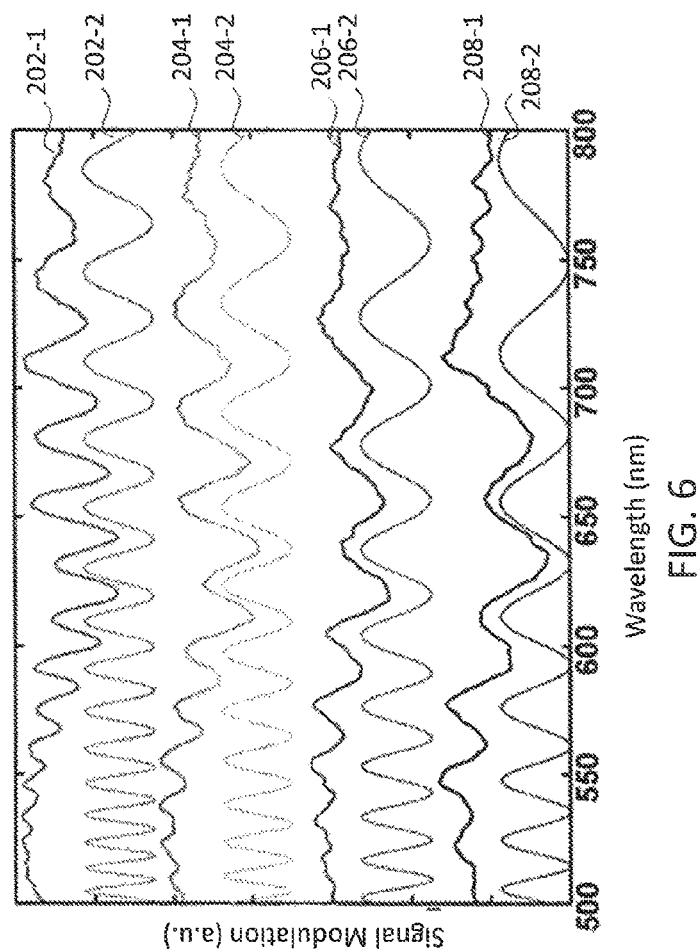
FIG. 6 illustrates SPP-mediated spectral interference introduced by SPP from first and second interfaces of a vertical Mach-Zehnder interferometer in accordance with FIG. 1.

The measurement results are shown by bold solid lines 202-1, 204-1, 206-1, and 208-1 in FIG. 6 in which spectral interference patterns can be observed under the TM illumination. The low frequency background and high frequency noise have been numerically filtered by Fast Fourier Transform ("FFT") (the low frequency cutoff was set at −2.896 $\mu m^{-1}$ and the high frequency cutoff was set at −217.196 $\mu m^{-1}$). Theoretical interference patterns were calculated in accordance with Equation 1 and are identified in FIG. 6 as reference numerals 202-2, 204-2, 206-2, and 208-2. Specifically, reference numerals 202-1 and 202-2 respectively correspond to the observed and simulated measurements for a slit-slit separation distance of 20.98 μm; reference numerals 204-1 and 204-2 respectively correspond to the observed and simulated measurements for a slit-slit separation distance of 15.73 μm; reference numerals 206-1 and 206-2 respectively correspond to the observed and simulated measurements for a slit-slit separation distance of 13.12 μm; and reference numerals 208-1 and 208-2 respectively correspond to the observed and simulated measurements for a slit-slit separation distance of 10.50 μm.

As shown in FIG. 6, the theoretical predictions are in accordance with the measurement thereby confirming the occurrence of SPP-mediated spectral interference from interfaces 106 and 108. Consequently, FIG. 6 demonstrates that air/Ag/glass interfaces are able to support several different interference patterns including, but not limited to, the SPP modes on interface 106 or interface 108, which can both interfere with free space light and introduce interference patterns with higher modulation frequencies. High frequency interference patterns were also observed in the wavelength region between 700 nm and 800 nm. The amplitude of the interference signal is optimized by balancing the intensity of the two SPP modes, which are related to the coupling efficiencies for the two SPP modes at interfaces 106 and 108 in VPMZI 100.

Figure 7A:
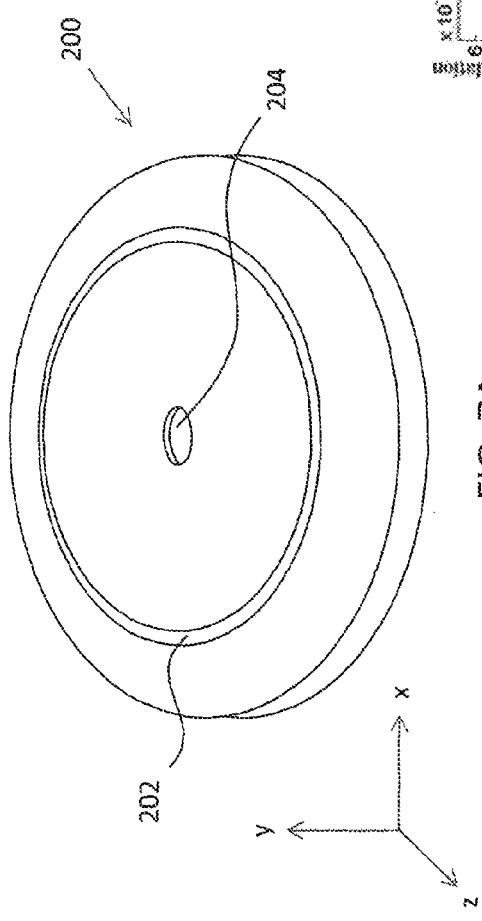
FIG. 7A illustrates one example of a circular plasmonic Mach-Zehnder interferometer.

FIG. 7A illustrates one example of a circular vertical Mach-Zehnder interferometer 200 having a multi-layered structure. Interferometer 200 includes a circular groove 202 forming a ring and an aperture 204 disposed at a center of the interferometer 200. In some embodiments, aperture has a circular shape and groove 202 is formed such that groove 202 and aperture 204 are concentrically formed. In some embodiments, groove 202 and aperture 204 are not concentrically formed.

Figure 7B:
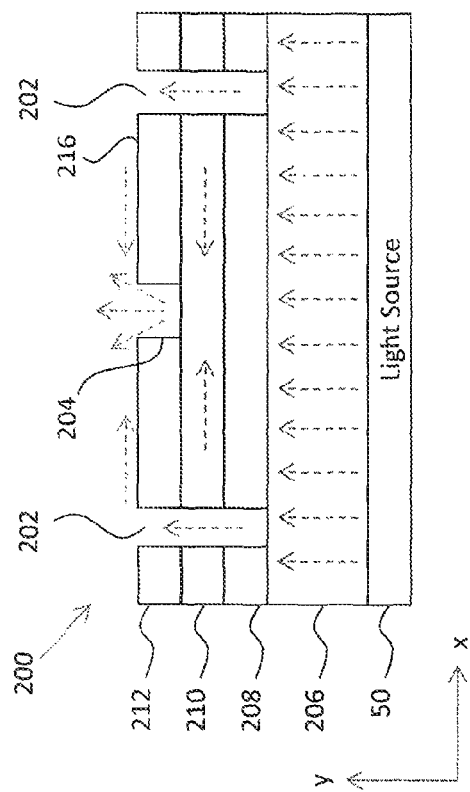
FIG. 7B is a cross-sectional view of one example of the plasmonic Mach-Zehnder interferometer illustrated in FIG. 7A.

As best seen in FIG. 7B, which provides a cross-sectional view of interferometer 200, multiple layers are formed over a substrate 206. In some embodiments, substrate 206 is formed of glass. Other materials may be used as substrate 206 including, but not limited to, quartz, transparent polymers (e.g., PDMS, fluorinated-ethylene propylene copolymer, epoxy resins), and other transparent semiconductor substrates as will be understood by one of ordinary skill in the art. A first conductive layer 208 is formed on an upper surface of substrate 206. Conductive layer can be a metallic material such as, for example, gold, silver, copper, and aluminum, or from graphene (for mid-infrared frequencies), to list but only a few possible materials. A dielectric layer 210 is formed on an upper surface of first conductive layer 208. Dielectic layer 210 may be selected based on the wavelengths that are to be used for data transmission or sensing. For example, dielectric layer 210 can include silicon and silicon dioxide for telecommunications applications, which typically utilize wavelengths of 1.33 μm or 1.55 μm. In embodiments utilizing visible wavelengths, dielectric layer 210 can include glass or a transparent polymer such as, for example, PDMS, fluorinated-ethylene propylene copolymer, and epoxy resins to name but only a few possibilities.

A second conductive layer 212 is formed on an upper surface of dielectric layer 210. In some embodiments, second conductive layer 212 is formed from the same material as first conductive layer 208. In some embodiments, conductive layer 212 is formed from a different material than the material from which first conductive layer 208 is formed.

Groove 202 is formed by milling (e.g., FIB milling), etching, or otherwise removing the metal-insulator-metal ("MIM") layers 208, 210, 212 from the upper surface of substrate 206 to form a ring, as illustrated in FIGS. 7A and 7B, such that the upper surface of substrate 206 is exposed. A milling, etching, or other process is used to form aperture 204, which is formed by removing a portion of second conductive layer 212 to expose an upper surface of dielectric layer 210.

The thickness of dielectric layer 210 can be selected such that interferometer 200 is tuned to support MIM modes are supported and other optical waveguide modes are not supported. Alternatively, the thickness of dielectric layer 210 can be selected such that both MIM and other optical waveguide modes are supported by interferometer 200.

As will be understood by one of ordinary skill in the art, the thickness of dielectric layer 210 is based on the material and wavelength for which the interferometer will be used. For example, in embodiment in which a $SiO_2$ layer is used as dielectric layer 210, the thickness of dielectric layer is less than or equal to 189 nm for a free-space wavelength of 700 nm.

In operation, a light source 50 directs light (shown in FIG. 7B as dashed arrows) towards the bottom surface of substrate 206. The light propagates in the y-direction through substrate 206 towards the upper surface of substrate 206. The propagating light is received within the opening of groove 202 where it excites one or more SPPs within dielectric layer 210, which forms the reference arm of interferometer 200. The SPPs propagate in the x- and z-directions (FIG. 7A), which are orthogonal to the y-direction, toward aperture 204. The light propagating through groove 202 also excites one or more single-interface SPPs (SI-SPP) at the upper surface of conductive layer 212, which is the interface 216 between second conductive layer 212 and the ambient surroundings. Interface 216 between conductive layer 212 and the air or ambient environment forms the sensing arm of interferometer 200.

When SPP modes excited by the groove 202 propagate to aperture 204, the SPP signals from the two optical branches (i.e., the sensing arm and the reference arm) interfere with each other and modulate the far-field scattering from the aperture 204, comprising a circular plasmonic MZI. Forming the first conductive layer 206 from an opaque material enables aperture 204 to not be illuminated by the incidence such that light source 50 can emit a wide-field light to excite the circular plasmonic MZI and a corresponding interference pattern can be observed. In some embodiments, light source 50 is a vertical-cavity surface-emitting laser ("VCSEL").

Figure 8:
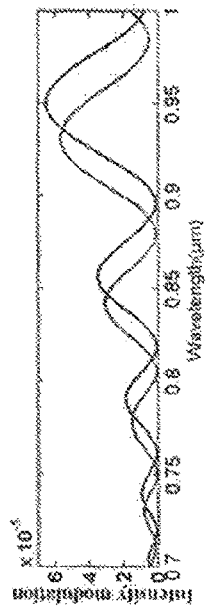
FIG. 8 is one example of numerical modeling for the interference signal of scatter light from the central aperture shown in FIGS. 7A and 7B.

The results of a FDTD simulation for an interferometer in accordance with FIGS. 7A and 7B are shown in FIG. 8. The width of groove 202 and aperture 204 were both 100 nm, with substrate 206 being glass, first and second conductive layers 208, 212 being gold, and dielectric layer being $SiO_2$. The thickness of the SiO$_2$ layer 210 was 100 nm, and the thicknesses of the first and second conductive layers 208, 212 was 300 nm.

As shown in FIG. 8, spectral interference patterns can be observed. When the refractive index of the top environment is changed from 1.33 to 1.34, one can see the spectral interference pattern shift accordingly between the two curves in FIG. 8 indicating that this novel circular design functions as a sensitive sensor. The structure may be designed as a two-dimensional array and will finally yield a promising device for low cost and portable multiplexed and parallel sensor device.

As stated above, interferometer 200 can be fabricated on a VCSEL array to realize a compact plasmonic interference modulated sensor array for real-time biomedical or environmental sensing (for example, in situ water monitoring and moisture or gas sensing). If the central dielectric material is replaced by electric, thermal or optical-modulated material, the interference modulation of the structure should also be useful for optical modulator and switches.

Figure 9C:
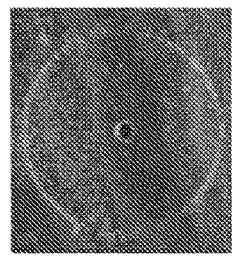
FIG. 9C is a scanning electron microscope image of a circular plasmonic interferometer in accordance with the embodiment illustrated in FIGS. 9A and 9B.
Figure 9A:
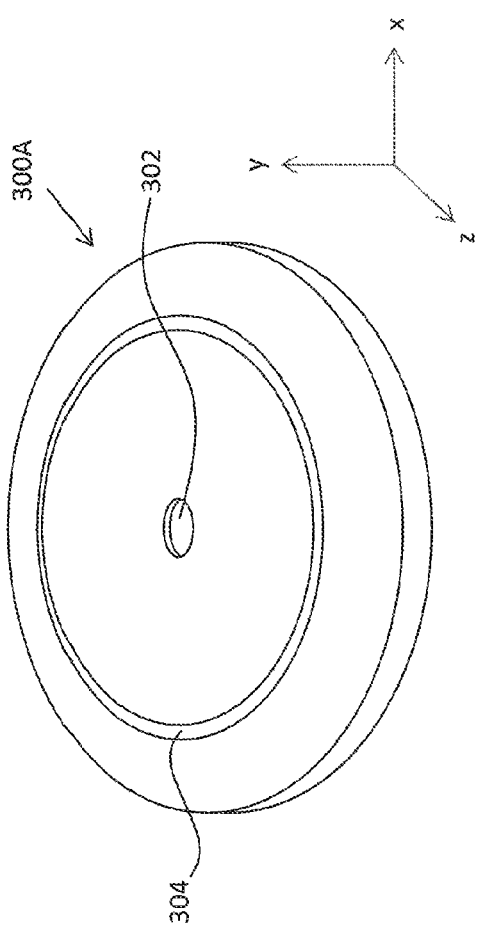
FIG. 9A illustrates one example of a circular plasmonic interferometer.
Figure 9B:
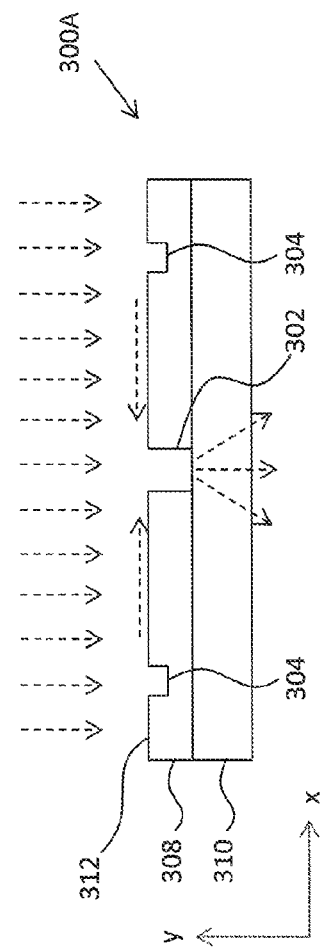
FIG. 9B is a cross-sectional view of the circular plasmonic interferometer illustrated in FIG. 9A.
Figure 10C:
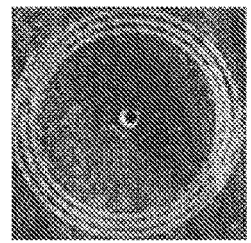
FIG. 10C is a scanning electron microscope image of a circular plasmonic interferometer in accordance with the embodiment illustrated in FIGS. 10A and 10B.
Figure 10A:
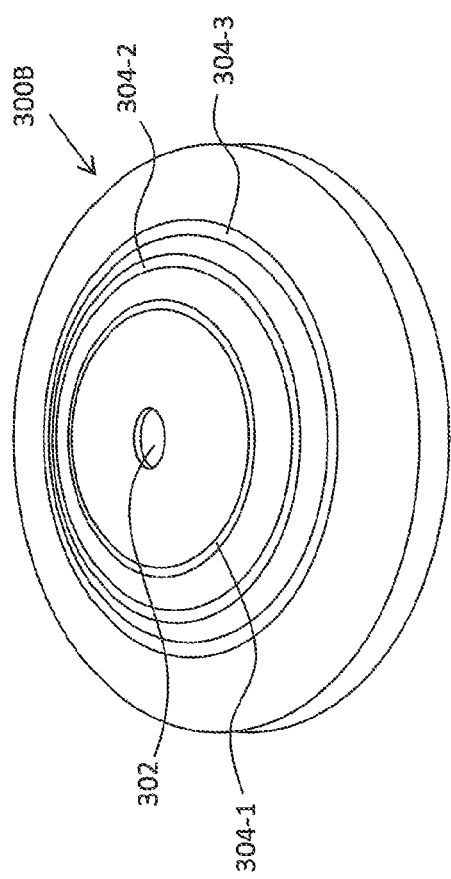
FIG. 10A illustrates another example of a circular plasmonic interferometer.
Figure 10B:
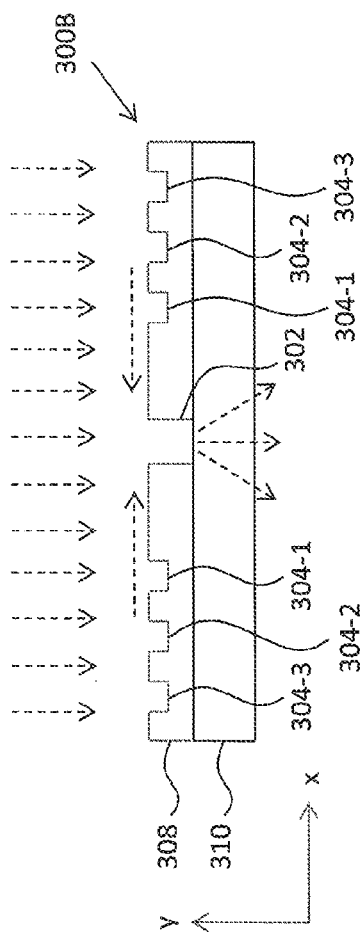
FIG. 10B is a cross-sectional view of the circular plasmonic interferometer illustrated in FIG. 10A.

FIGS. 9A and 10A are isometric views of examples of a vertical plasmonic interferometers 300A and 300B, respectively. The difference between interferometers 300A and 300B are the number of circular grooves as described in greater detail below. FIGS. 9B and 10B are cross-sectional views of interferometers 300A and 300B, respectively, and FIGS. 9C and 10C are scanning electron microscope images of the respective interferometers formed using gold film disposed on a glass substrate.

Referring first to FIGS. 9A and 9B, interferometer 300A includes an aperture 302 around which a groove 304 is formed such that a circular ring is defined in conductive layer 308. As best seen in FIG. 9B, interferometer 300A is a two-layer structure comprising a transparent substrate 306 over which a conductive layer/film 308 is disposed. In some embodiments, transparent substrate 306 is formed from glass, Quartz, or other transparent semiconductor material. Conductive layer 308 can be formed from a metallic material including, but not limited to, silver, gold, gold, silver, copper, and aluminum, or from graphene, to name only a few possible materials.

Conductive layer 308 is patterned such that aperture 302 extends through conductive layer 308 to expose a portion of the upper surface of substrate 310 thereby allowing light to propagate therethrough. As will be understood by one of ordinary skill in the art, aperture 302 can be formed by milling, etching, or other suitable process to create aperture 302. Circular groove 304 is formed to a specific depth from the upper surface of conductive layer 308 such that groove 304 does not extend to the upper surface of substrate 310.

Turning now to FIGS. 10A and 10B, interferometer 300B also includes a substrate 310 over which a conductive layer 308 is formed. Aperture 302 extends through the entirety of conductive layer 308 such that an upper surface of substrate 310 is exposed. Grooves 304-1, 304-2, and 304-3 (collectively "grooves 304") are formed in an upper portion of conductive layer 308. In some embodiments, grooves 304 are concentric and equally spaced from one another as well as being concentric with aperture 302.

In operation, light propagates towards the upper surface of conductive layer 308 (i.e., in the negative y-direction shown in FIGS. 9B and 10B). The propagating light excites SPPs at the interface 312 between the upper surface of conductive layer 308 and the ambient environment. The excited SPPs travel in the x- and z-directions either towards or away from aperture 302. At aperture 302, the SPPs constructively and destructively interfere with one another and with the light that is directly transmitted through aperture 302. The SPPs are rescattered at aperture 302 and modify the far-field scattering.

Figure 12:
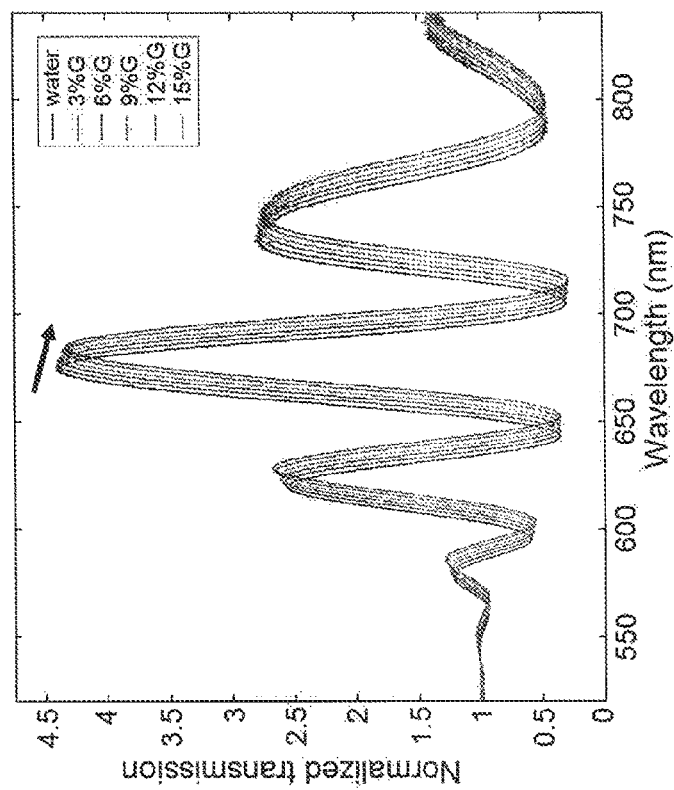
FIG. 12 illustrates experimental interference signals of an interferometer in accordance with FIGS. 10A-10C for liquids having different refractive indices.
Figure 11:
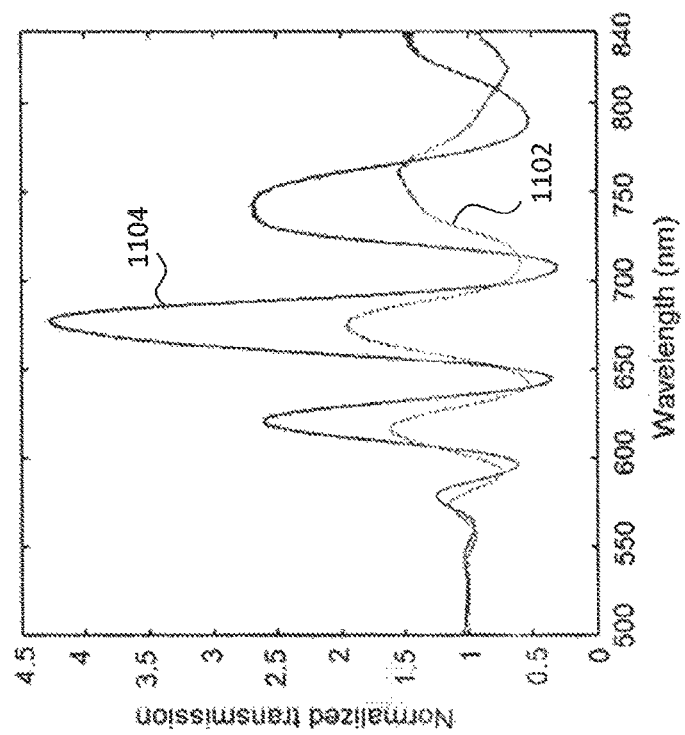
FIG. 11 illustrates experimental interference signals of interferometers in accordance with FIGS. 9A-9C and 10A-10C.

FIG. 11 is a graph illustrating the interference signal for an interferometer in accordance FIGS. 9A-9C (line 1102) and the interference signal (line 1104) for an interferometer in accordance with FIGS. 10A-10C. The interference signals 1102, 1104 illustrated in FIG. 11 are based on experimental results. As shown in FIG. 11, the modulation depth of the interference patter increases by fabricating multiple circular grooves. FIG. 12 illustrates experimental interference signals for liquids having different refractive indices as sensed by an interferometer in accordance with FIGS. 10A-10C.

Figure 13C:
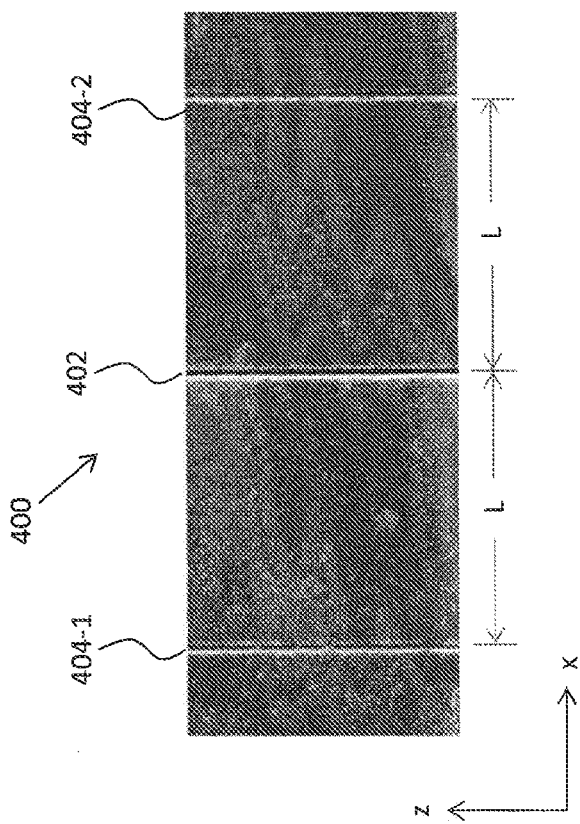
FIG. 13C is a scanning electron microscope image of a plasmonic interferometer in accordance with the embodiment illustrated in FIGS. 13A and 13B.

Vertical plasmonic interferometers can also be implemented with non-circular layouts. For example, FIGS. 13A-13C illustrate one example of a rectangular vertical plasmonic slit-groove interferometer 400. Interferometer 400 include an aperture 402 taking the form of an elongate slit that is disposed between and parallel to a pair of parallel grooves 404-1, 404-1 (collectively "grooves 404"). A transparent substrate 406 supports a conductive or metallic layer 408, which is formed over an upper surface of substrate 406.

In some embodiments, substrate 406 is formed of a transparent material that enables light to propagate through substrate 406. Examples of such materials include, but are not limited to, glass, quartz, transparent polymers (e.g., PDMS, fluorinated-ethylene propylene copolymer, epoxy resins), and other transparent semiconductor materials. In some embodiments, substrate 406 has a thickness of 150 μm up to several centimeters.

Conductive layer 408 is formed on an upper surface of transparent substrate 406. As described above, conductive layer 408 may be formed using gold, silver, copper, aluminum, or other metallic material. Aperture/slit 402 and grooves 404 may be formed in conductive layer 408 by milling, etching, or other suitable method. Slit 402 is formed such that conductive layer 408 is removed to expose the upper surface of substrate 406. In some embodiments, slit 406 extends entirely across substrate 406. Grooves 404 are formed in conductive layer 408 to a depth from the upper surface of conductive layer that is less than a thickness of conductive layer 408 such that the upper surface of substrate 406 is not exposed.

In operation, light is directed towards the bottom surface of transparent layer 406. Being transparent, light propagates through layer 406 towards the bottom surface of conductive layer 408 (i.e., in a positive y-direction). The opaque conductive layer 408 blocks the propagating light except for the light received along slit 402, which then propagates along slit 402 in the y-direction. The propagating light excites SPPs modes at interface 410 between the upper surface of conductive layer 408 and ambient air or fluid with which the upper surface of conductive layer 408 is in contact. SPP modes travel along interface 410 perpendicular to the direction in which the light propagates (i.e., in the x-direction). At least a portion of the SPP modes are reflected back toward slit 402 by grooves 404 where they interfere with light directly transmitted through slit 402.

A vertical plasmonic interferometer in accordance with the embodiment illustrated in FIGS. 13A and 13B was fabricated and tested. FIG. 13C is a scanning electron microscope image of such a plasmonic interferometer. The fabricated interferometer included a 350 nm thick silver film evaporated on a glass microscope slide. Slit 402 and grooves 404 were formed using FIB milling such that slit 402 and two flanking grooves 404 were 30 μm in length. The width (x-direction dimension) of slit 402 was 100 nm, and the width of grooves 404 were 120 nm. The depth of grooves 404 was approximately 70 nm as measured by atomic force microscopy (AFM) (NT-MDT Solver NEXT). Slit 402 was located at the center of grooves 404 with a slit-groove distance of L as shown in FIG. 13C. For one experiment, L was equal to 5.1 µm.

After the FIB milling, plasma-enhanced chemical vapor deposition ("PECVD") was used to deposit a 3-5 nm thick silicon dioxide film on top of the silver surface. This chemically stable dielectric film functioned as a protection layer to enhance biocompatibility and chemical stability of the silver-based device, particularly in aqueous solutions.

The structure was illuminated through the substrate as illustrated in FIG. 13B. Under the TM-polarized illumination (with the electric field perpendicular to the long axis of slit 402), SPPs were launched at the central slit 402, and propagated toward grooves 404 where they were partially reflected back. The reflected SPPs were then scattered at slit 402 and interfered with the light directly transmitted through the slit 402. The SPP-mediated scattered light was collected by an ×40 objective and coupled into a spectrometer.

Figure 14:
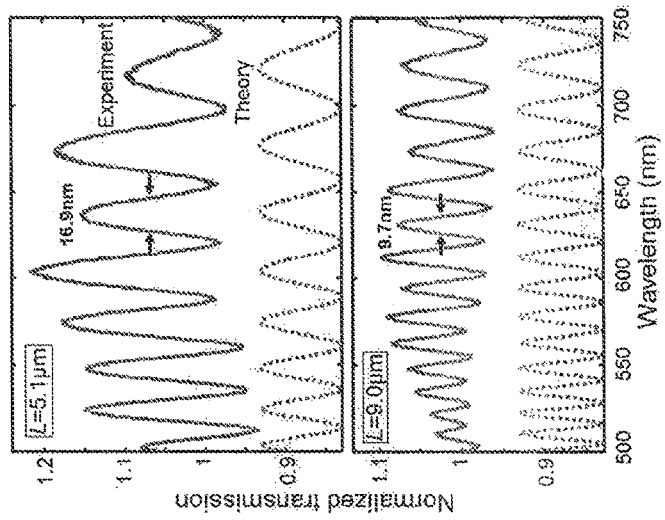
FIG. 14 illustrates the experimental interference patterns and theoretical predications for a plasmonic interferometer in accordance with FIGS. 13A-13C in an air environment.

The solid curves in FIG. 14 show the experimental spectra of two interferometers with L of 5.1 and 9.0 µm, respectively, in an air environment. A smoothing algorithm was not applied to the experimental spectra. Data were normalized by the transmission spectrum of an identical reference single slit milled on the same sample. One can see fast spectral oscillations with narrow peaks and valleys resulting from the constructive and destructive interference between the light transmitted directly through slit 402 and SPPs propagating between grooves 404 and slit 402. The scattered light intensity from the central slit 402 carries the information of the relative phase difference between SPPs and the incident beam, which is highly sensitive to the surface refractive index change and can be employed for sensing applications. To verify this SPP-light interference hypothesis, theoretical interference patterns were calculated using the following equation:

$$\frac{I}{I_0} = 1 + \frac{E_{spp}^2}{E_{free}^2} + 2\frac{E_{spp}}{E_{free}}\cos\left(\frac{4\pi L}{\lambda}n_{spp} + \varphi_0\right) \quad \text{Eq. (4)}$$

The $E_{free}$ and $E_{spp}$ are the field amplitudes of directly transmitted light and SPP modes, respectively; $n_{spp}(\lambda)=\text{Re}((\in_m n^2/(\in_m+n^2))^{1/2})$ is the effective refractive index of SPPs at the metal/dielectric interface; $\in_m$ is the metal permittivity; n is the refractive index of the dielectric material on top of the metal surface; and $\phi_0$ is an additional constant phase shift. The dotted curves in FIG. 14 show the calculated interference patterns using the cosine term in Equation 4. The calculated oscillation frequencies and spectral positions of the peaks and valleys agree very well with the experimental data, indicating that the interference between directly transmitted light and propagating SPPs can be observed using the experimental setup. The observed narrow linewidths of the interference oscillations can be used for enhanced refractive index sensing.

For example, the intensity of the transmitted light at a specific wavelength depends on the phase difference between SPPs and free-space light through the term ($4\pi L n_{spp}/\lambda+\phi_0$) of Equation 4. The phase difference can be modulated by the surface refractive index change or biomolecule adsorption at the sensor interface. A spectral shift of the interference pattern can be observed for broadband illumination. By setting the term $n_{spp}/\lambda$ to constant in Equation 4, the refractive index sensitivity of this plasmonic sensor can be derived as $$S = \left|\frac{\Delta\lambda}{\Delta n}\right| \approx \lambda\left(\frac{n_{spp}}{n}\right)^3 / \left(n_{sp} - \lambda\frac{dn_{spp}}{d\lambda}\right) \quad \text{Eq. (5)}$$

Equation 5 predicts that S is approximately 481 nm/RIU in water environment at a wavelength around 650 nm. The unique advantage of this sensing scheme is the ultra-narrow linewidth of the interference oscillation. The peak linewidth, $\delta\lambda$, is defined as half of the oscillation period, P, and can be described by the following equation:

$$\delta\lambda = \frac{P}{2} \approx \lambda^2/4L\left(n_{spp} - \lambda\frac{dn_{spp}}{d\lambda}\right) \quad \text{Eq. (6)}$$

Using Equation 6, the peak linewidths are calculated to be 16.3 nm ($\lambda \sim 636.1$ nm) and 9.1 nm ($\lambda \sim 631.1$ nm) for interferometers with L=5.1 and 9.0 µm in air, respectively, which corresponds to the experimental results illustrated in FIG. 14. Equation 6 also predicts that further decreased linewidths can be achieved in aqueous environment for larger L and shorter wavelengths. To evaluate the overall performance of plasmonic sensors more precisely, we calculate the sensor figure of merit FOM=S/$\delta\lambda$, which is defined as the refractive index sensitivity divided by the sensing peak linewidth. FOM is widely accepted as an appropriate parameter to evaluate and compare the overall plasmonic sensor performance by taking into consideration both sensor sensitivity and sensing peak sharpness. The theoretical FOM of this plasmonic interferometer is derived as follows:

$$FOM = \frac{S}{\delta\lambda} = \frac{4L}{\lambda}\left(\frac{n_{spp}}{n}\right)^3 \quad \text{Eq. (7)}$$

Equation 7 provides that high FOMs are achievable using the proposed sensing scheme. For example, the calculated FOM value reaches 65 for an interferometer with L=9.0 µm at $\lambda$=650 nm, which surpass previous EOT-based sensors with a typical FOM value of 23 and nanoparticle-based LSPR sensors with FOMs typically <10.

Figures 15, 16:
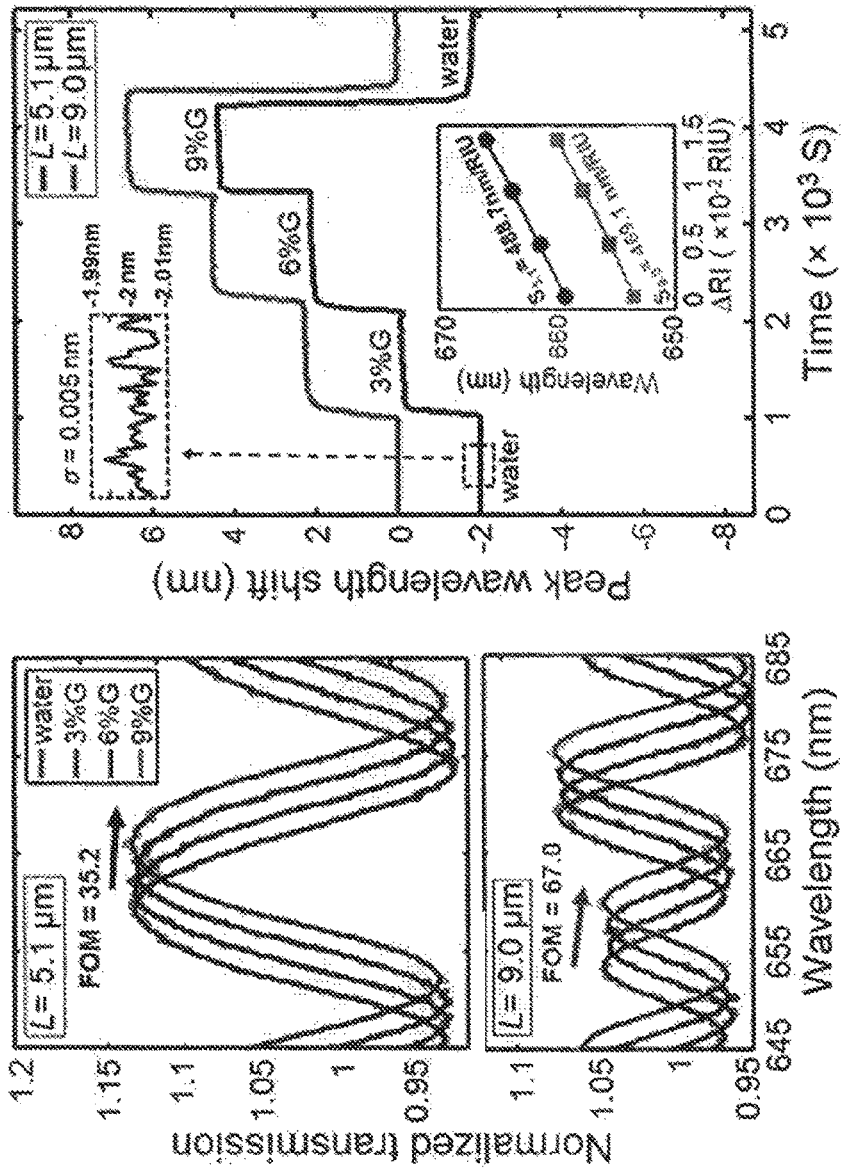
FIG. 15 illustrates the measured interference patterns of a plasmonic interferometer in accordance with FIGS. 13A-13C for water 3%, 6%, and 9% glycerol-water solutions.
FIG. 16 illustrates the monitored peak positions for two interferometers in accordance with FIGS. 13A-13C as a function of time.

The interferometer 400 was integrated with a polydimethylsiloxane ("PDMS") microfluidic flow cell and injected a series of glycerol-water solutions of varying glycerol concentration to tune the liquid refractive index to experimentally demonstrate the theoretically predicted sensor performance. As shown in FIG. 15, the interference patterns of interferometers with two different L both red-shift, as indicated by the directions of the arrows, as the liquid refractive index increases. The peak positions were extracted using a Lorentzian fitting method and plotted in FIG. 16 as a function of time. For clarity, the sensor response of the interferometer with L=5.1 µm was vertically displaced by 2 nm in this plot.

From FIG. 16, both interferometers exhibit stable peak wavelengths at each glycerol concentration and the peak shifts were approximately proportional to the increase in glycerol concentration. The sensing peaks return to their initial spectral positions for both interferometers with the final DI water injection. The lower inset of FIG. 16 shows the peak positions as a function of the liquid refractive index. The solid lines are the linear fits to the experimental data, providing sensitivities of the two sensors. For plasmonic interferometers with L=5.1 and 9.0 µm, the measured sensitivities are 488.7 and 469.1 nm/RIU, respectively, with peak linewidths of 13.9 and 7.0 nm, and FOMs of 35.2 and 67.0, respectively, all in good agreement with the theoretical predictions (see Table 1).

TABLE 1

| L (µm) | Peak λ (nm) | Sensitivity (nm/RIU) | Linewidth (nm) | FOM |
|---|---|---|---|---|
| 5.1 | 659.4 | 488.7 | 13.9 | 35.2 |
|  |  | 484.7 | 13.4 | 36.2 |
| 9.0 | 653.6 | 469.1 | 7.0 | 67.0 |
|  |  | 482.2 | 7.4 | 65.2 |

As shown in the upper inset of FIG. 16, the standard deviation (a) of the monitored peak wavelength is around 0.005 nm, which corresponds to a sensor refractive index resolution of $1 \times 10^{-5}$ RIU [i.e., 0.005 nm/(488.7 nm/RIU)]. The sensor resolution was measured from a single plasmonic interferometer with a footprint of $30 \times 10$ µm$^2$. Previous EOT-based plasmonic sensors were able to achieve similar enhanced sensor resolutions by fabricating nano-aperture arrays over millimeter or centimeter-sized areas, primarily to provide a large photon flux to enhance the sensor signal-to-noise ratio. Compared with these large-area nano-patterned sensors, the disclosed plasmonic sensor has a smaller sensor footprint and advantageously enables multiplexing.

The enhanced sensor performance and small footprint of the disclosed vertical plasmonic interferometers permit sensitive multiplexed sensing with high packing density and enables sensor integration with compact microfluidic devices that require small reagent volumes. While the measured high FOM value of 67 could in principle be further increased for larger values of L and shorter wavelengths, the spectral modulation depth decreases under these conditions due to the higher SPP propagation loss, limiting improvements in sensor performance.

The FOM and sensor resolution of the plasmonic interferometer that was experimentally fabricated and tested can be improved by utilizing one or more of the following techniques. First, SPP reflection efficiency at the two grooves can be enhanced by improving the quality of the fabricated two grooves (e.g., using Ag—Al double metal layers with the bottom Al layer as a slow etch rate FIB stop to precisely and uniformly control the fabricated groove depth). Second, SPP propagation loss can be reduced by employing an ultrasmooth metal film obtained by template stripping. Third, the sensor noise level could be further reduced by adding a temperature controller for the sensor chip and using a detector with a higher saturation level.

Figure 17:
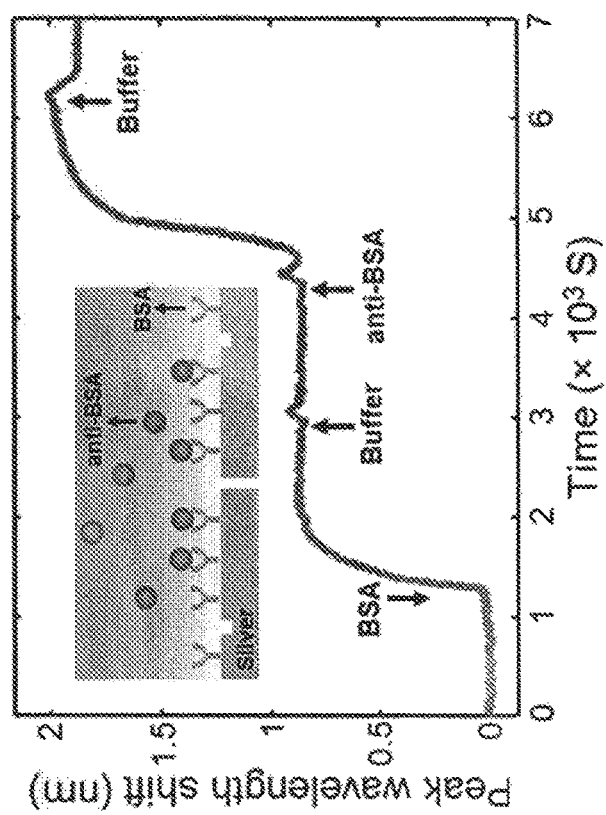
FIG. 17 illustrates real-time sensor response for an interferometer in accordance with FIGS. 13A-13C upon BSA adsorption to the sensor surface and subsequent specific protein binding between BSA and anti-BSA.

The binding between BSA and anti-BSA was monitored in real-time using the fabricated inteferometer for which L=5.1 µm to demonstrate the feasibility of the sensing platform to detect biomolecular binding events. The results of the binding between BSA and anti-BSA are illustrated in FIG. 17 in which the arrows indicate the injections of analytes and buffer solutions. The upper inset of FIG. 17 shows a schematic of anti-BSA binding to BSA immobilized on the sensor surface. The microfluidic channel was first injected with a 10 mM HEPES buffer for 25 minutes to clean the sample surface and define the baseline of the experiment. A 500 µg/mL BSA solution in HEPES was introduced into the channel to functionalize the metal surface with a BSA monolayer, which leads to a 0.9 nm shift of the peak wavelength (see the first signal change at the time of 1200 s in FIG. 17).

A subsequent 25 min buffer rinse had little effect on the peak wavelength. A 42 µg/mL anti-BSA solution was injected into the channel and followed by a buffer rinse to wash out the unbound anti-BSA molecules. The small spikes observed at time t=3000 s and 4500 s are measurement artifacts caused by exchanging syringes. The specific binding between BSA and anti-BSA corresponds to a peak wavelength shift of 1 nm. The observed 0.9 nm peak shift upon saturation coverage of BSA on the sensor surface corresponds to an effective protein layer thickness of 0.92 nm (assuming the refractive index of BSA is 1.57).

By use of the density of BSA (1.3 g/cm$^3$), the BSA surface concentration is calculated to be $1.2 \times 10^{-7}$ g/cm$^2$ (i.e., 1.3 g/cm$^3 \times 0.92$ nm). The surface coverage resolution of the sensing system can be calculated using Equations 5-7. As described above, the minimum resolvable peak wavelength shift of fabricated sensor was 0.005 nm, which corresponds to an effective BSA layer thickness of 0.0051 nm. This sensor resolution in effective layer thickness can be converted to a protein coverage resolution by multiplying the BSA bulk density. The surface coverage resolution of the fabricated sensing system is 6.6 pg/mm$^2$ (i.e., 1.3 g/cm$^3 \times 0.0051$ nm).

Real-time and sensitive multiplexed sensing experiments by using a CCD camera and a narrow band light source were also performed. A 4×3 microarray of the slit-groove plasmonic interferometers were fabricated and are illustrated in FIG. 18A. Interferometers in the first and third (second and fourth) columns of the microarray have a groove-slit distance, L, of 5.1 (5.2) µm. FIG. 18B is a scanning electron microscope image of the fabricated microarray, and FIG. 18C is a CCD image of one of the plasmonic interferometers. Each interferometer had a footprint of around 300 µm$^2$ with the center-to-center distance between each sensing element of 50 µm, giving a potential packing density of $4 \times 10^4$ sensors per cm$^2$. Such a dense packing capability of the plasmonic sensing scheme enables low-cost, label-free, and high-throughput on-chip microarray applications.

The fabricated microarray was illuminated through the substrate using a white light source passing through an optical band-pass filter centered at 655 nm with a 12 nm bandwidth. The transmitted light from the 12 interferometers was then collected simultaneously by a 40× microscope objective and imaged onto a CCD camera. The transmitted light intensity change from each interferometer is determined by two factors: (1) the spectral shift due to the refractive index change, and (2) the slope of the transmission spectrum at the illumination wavelength. Accordingly, to achieve the optimized sensing performance, the slit-groove distance is tuned to spectrally shift the interference pattern and position its high-slope region at the illumination wavelength.

Figures 19, 20:
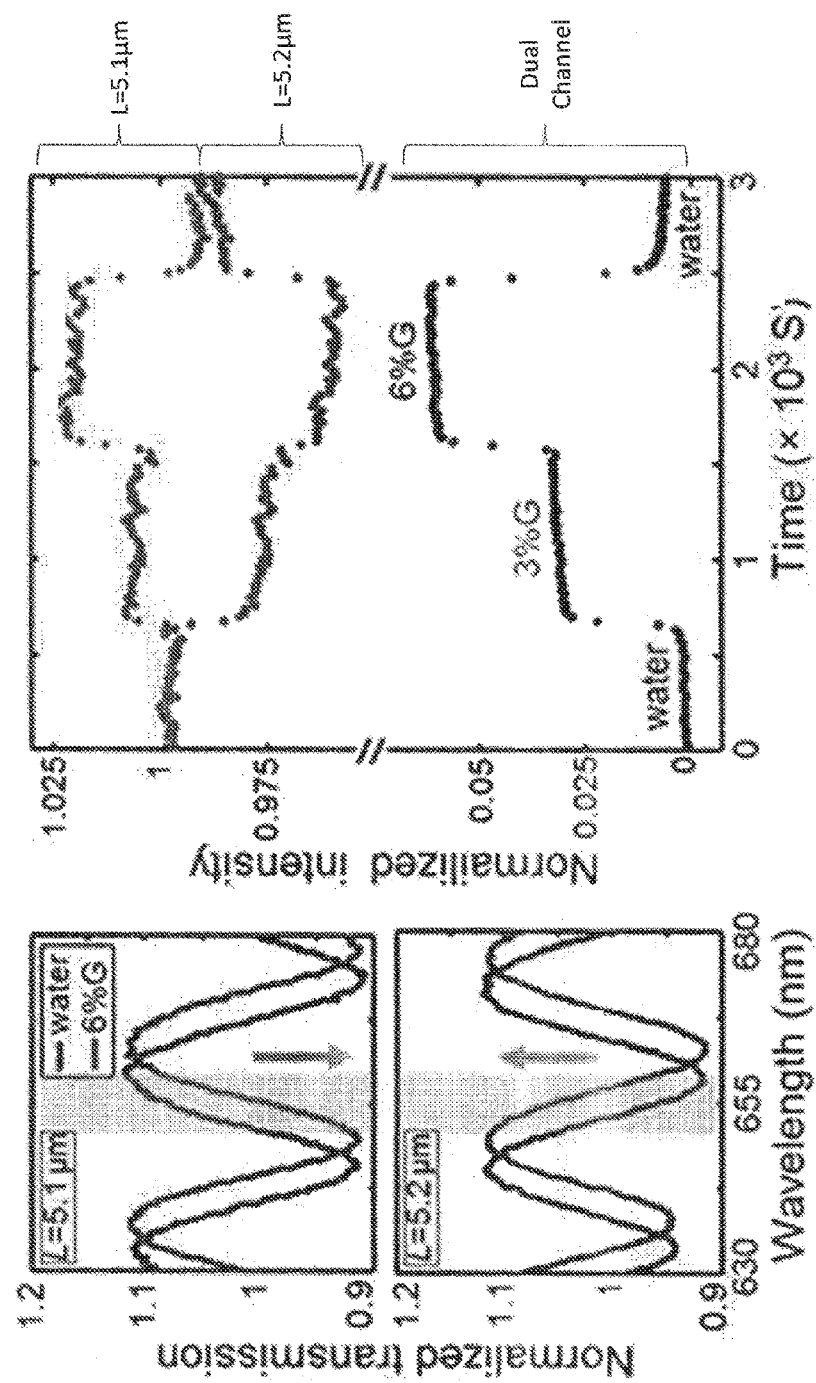
FIG. 19 illustrates the transmission spectra of interferometers in accordance with FIGS. 13A-13C having two different slit lengths.
FIG. 20 illustrates the real-time measurements of the normalized transmitted intensities from interferometers in accordance with 13A-13B having two different slit lengths.

Plasmonic interferometers with L of 5.1 and 5.2 µm were used in the measurement, and their transmission spectra are shown in FIG. 19. The central shaded regions indicate the spectral range of the incident light. The interference patterns red-shift with the increase of the liquid refractive index, and the transmitted intensity could either increase or decrease, depending on negative or positive slope of the transmission spectrum. The dots in FIG. 20 present real-time experimental measurements of the transmitted intensities from two interferometers indicated by boxes 1802 and 1804 in FIG. 18A, respectively. As a series of glycerol-water solutions with varying glycerol concentration were injected into the channel, the sensor transmitted intensities either decrease (for L=5.1 µm) or increase (for L=5.2 µm) in agreement with the predictions. Following the 6% glycerol test, DI water was again introduced into the channel, returning the transmitted intensities to their initial levels and validating the reliability of the sensing performance. The standard deviation of the measured light intensity determines the refractive index resolution of this intensity-interrogated sensor, which are calculated to be $4 \times 10^{-4}$ RIU (L=5.2 µm) and $3 \times 10^{-4}$ RIU (L=5.1 µm) for two interferometers, respectively.

A dual-channel differential method can reduce the effects of noise from mechanical vibrations and light intensity fluctuations. As shown in FIG. 19, two interferometers were designed different lengths, i.e., L=5.1 and 5.2 µm, which exhibit similar initial transmitted intensities but have positive and negative intensity-change sensitivities. As a result, a signal arising from surface refractive index change shifts the transmitted intensities of these two sensors in two different directions (that is transmission increase or decrease), while unwanted signal from light intensity fluctuations and mechanical vibrations change two transmitted intensities in the same direction.

By monitoring the difference between the transmitted intensities from two interferometers in real time, this method not only approximately doubles the sensor response, but also effectively subtracts the background noises and the baseline drift (see dots in dual channel section of FIG. 20). The resulting refractive index sensing resolution decreases to $5 \times 10^{-5}$ RIU, which is six times smaller than that of the single channel sensing method ($3 \times 10^{-4}$ RIU for a interferometer with L=5.1 µm).

Further improvement in sensor resolution is also possible by using similar methods as discussed above. For example, metal films with ultra-smooth surfaces and precisely fabricated grooves 404 could increase the interference modulation depth and thus improve the sensitivity of this intensity-interrogated multiplexed sensor. Additionally, an intense and highly stable laser source may further reduce the light source fluctuation and therefore improve the sensor resolution compared to using a halogen lamp.

Figure 21A:
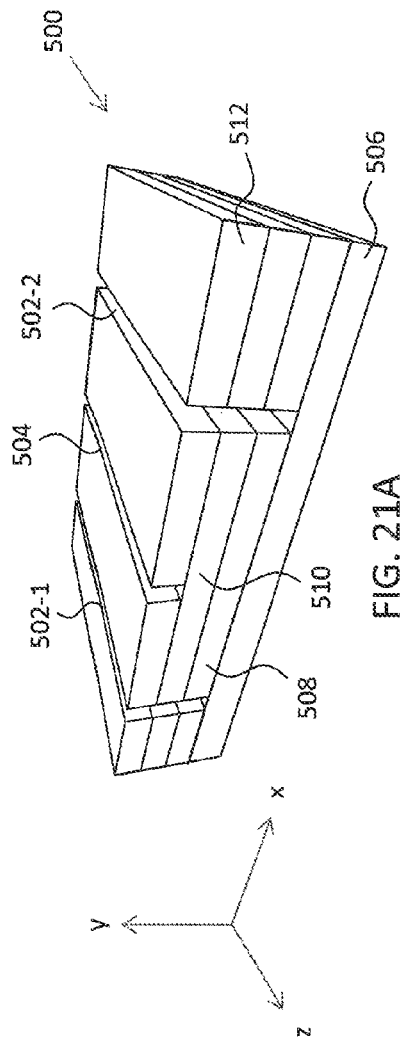
FIG. 21A is an isometric view of another example of a vertical plasmonic interferometer.
Figure 21B:
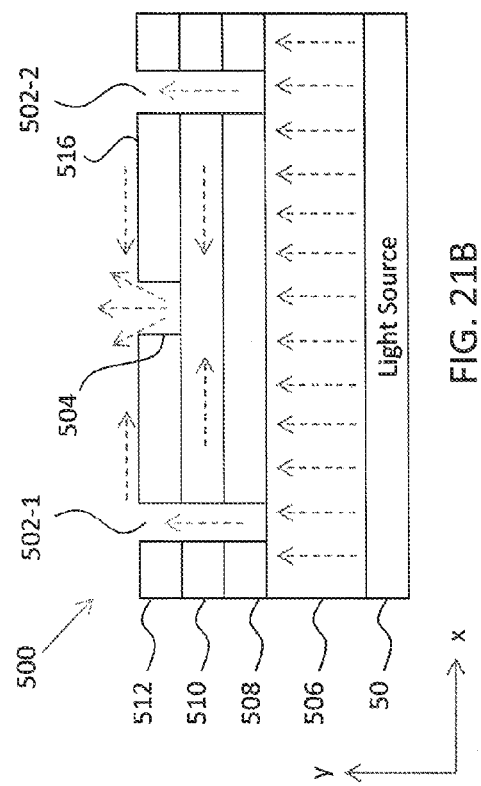
FIG. 21B is a cross-sectional view of the vertical plasmonic interferometer illustrated in FIG. 21A.

FIGS. 21A and 21B illustrate another embodiment of a vertical plasmonic interferometer 500. Interferometer 500 is a rectangular embodiment of the circular interferometer 200 described above with respect to FIGS. 7A and 7B. As shown in FIG. 21A, interferometer 500 includes first and second grooves 502-1, 502-2 (collectively "grooves 502") and an aperture 504 disposed between grooves 502.

As best seen in FIG. 21B, interferometer 500 includes a plurality of layers formed over substrate 506. In some embodiments, substrate 506 is formed of glass, although other materials, including, but not limited to, quartz, transparent polymers (e.g., PDMS, fluorinated-ethylene propylene copolymer, epoxy resins), and other transparent semiconductor substrates may be used as substrate 506. A first conductive layer 508 is disposed on an upper surface of substrate 506. A dielectric layer 510 is formed on an upper surface of first conductive layer 508, and a second conductive layer 512 is disposed over an upper surface of dielectric layer 510.

First and second conductive layers 508, 512 can be a metallic material such as, for example, gold, silver, copper, and aluminum, or be graphene, to list only a few possible materials. In some embodiments, first and second conductive layers 508, 512 are formed from the same material. In some embodiments, first and second conductive layers 508, 512 are formed from different materials.

Dielectic layer 510 may be selected based on the wavelengths that are to be used for data transmission or sensing. For example, dielectric layer 510 can include silicon and silicon dioxide for telecommunications applications, which typically utilize wavelengths of 1.33 µm or 1.55 µm. In embodiments utilizing visible wavelengths, dielectric layer 510 can include glass or a transparent polymer such as, for example, PDMS, fluorinated-ethylene propylene copolymer, and epoxy resins to name but only a few possibilities.

Grooves 502 are formed by milling (e.g., FIB milling), etching, or otherwise removing MIM layers 508, 510, 512 from the upper surface of substrate 506 to form a pair of parallel lines that extend from one side of substrate 506 to an opposite side of substrate 506, as best seen in FIG. 21A, such that the upper surface of substrate 506 is exposed (FIG. 21B). A milling, etching, or other process is used to form aperture 504, which is formed by removing a portion of second conductive layer 512 to expose an upper surface of dielectric layer 510.

The thickness of dielectric layer 510 can be selected such that interferometer 500 is tuned to support MIM modes are supported and other optical waveguide modes are not supported. Alternatively, the thickness of dielectric layer 510 can be selected such that both MIM and other optical waveguide modes are supported by interferometer 500.

As will be understood by one of ordinary skill in the art, the thickness of dielectric layer 210 is based on the material and wavelength for which the interferometer will be used. For example, in embodiment in which a $SiO_2$ layer is used as dielectric layer 210, the thickness of dielectric layer is less than or equal to 189 nm for a free-space wavelength of 700 nm.

In operation, a light source 50 directs light (shown in FIG. 21B as dashed arrows) towards the bottom surface of substrate 506. The light propagates in the y-direction through substrate 506 towards the upper surface of substrate 506. The propagating light is received within the opening or groove 502 where it excites one or more SPPs within dielectric layer 510, which forms the reference arm of interferometer 500. The SPPs propagate in the x- and z-directions (FIG. 21A), which are orthogonal to the y-direction, toward aperture 504. The light propagating through groove 502 also excites one or more SI-SPPs (SI-SPP) at the upper surface of conductive layer 512, which is the interface 516 between second conductive layer 512 and the ambient surroundings. Interface 516 between conductive layer 512 and the air or ambient environment forms the sensing arm of interferometer 500.

When SPP modes excited by the groove 502 propagate to aperture 504, the SPP signals from the two optical branches (i.e., the sensing arm and the reference arm) interfere with each other and modulate the far-field scattering from the aperture 504, comprising a plasmonic MZI. Forming the first conductive layer 506 from an opaque material enables aperture 504 to not be illuminated by the incidence such that light source 50 can emit a wide-field light to excite the plasmonic MZI and a corresponding interference pattern can be observed. In some embodiments, light source 50 is a VCSEL, although one of ordinary skill in the art will understand that other light sources may be used.

Combining surface plasmon modes and the MZI concept into a single device as described above advantageously extends single point sensing to two-dimensional multiplexed sensor arrays, which should be promising for low cost and portable parallel sensing applications. The vertical plasmonic interferometers advantageously provide high sensitivity for optical sensing that has the potential for a one-to-two order-of-magnitude improvement over conventional nanoaperture arrays. Additionally, compact sensing packages can be integrated into sensitive biosensing platforms and subwavelength optics on a chip. For example, vertical plasmonic interferometers can be integrated into a microfluidic channel to observe SPP interference in liquid and gaseous environments.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A plasmonic interferometer sensor comprising:
   a transparent substrate; and
   a first conductive layer disposed over an upper surface of the transparent substrate, the first conductive layer defining at least one groove inwardly extending along an upper surface and defining an aperture that is spaced apart from the at least one groove,
   wherein an interface between the upper surface of the first conductive layer and an ambient medium defines a first optical branch along which surface plasmon polariton modes are excited in response to at least partially coherent light being received by the optical device;
   a second conductive layer disposed over and directly in contact with the upper surface of the transparent substrate; and
   a dielectric layer disposed between the first and second conductive layers such that a lower surface of the dielectric layer is directly in contact with an upper surface of the second conductive layer, and an upper surface of the dielectric layer is directly in contact with a lower surface of the first conductive layer;
   wherein the at least one groove defines a ring in the first conductive layer, and the aperture has a circular shape;
   wherein the at least one groove extends entirely through the dielectric layer and through the first and second conductive layers such that a portion of the upper surface of the transparent substrate is exposed, and wherein the aperture extends entirely through the first conductive layer such that a portion of the upper surface of the dielectric layer is exposed.

2. The plasmonic interferometer sensor of claim 1, wherein the dielectric layer defines a second optical branch along which surface plasmon polariton modes are excited in response to at least partially coherent light being received by the optical device.

3. The plasmonic interferometer sensor of claim 2, wherein the first optical branch is a sensing arm of the optical device and the second optical branch is a reference arm of the optical device.

4. The plasmonic interferometer sensor of claim 1, wherein the at least one groove includes a plurality of concentric grooves each being concentric with the aperture.

5. A vertical plasmomic interferometer sensor comprising:
   a substrate having first and second opposed surfaces and being configured to transmit light received at the first surface to the second surface and to transmit light received at the second surface to the first surface;
   a first conductive layer having a third surface that is disposed on an opposite side of the first conductive layer than a fourth surface, the fourth surface defining an interface with an ambient medium, the first conductive layer defining at least one groove inwardly extending along the fourth surface and defining an aperture that is spaced apart from the at least one groove,
   wherein the interface between the fourth surface and the ambient medium defines a first optical branch along which surface plasmon polariton modes are excited in response to at least partially coherent light being received by the vertical plasmonic interferometer;
   a second conductive layer disposed over and directly in contact with the second surface of the substrate, the second conductive layer comprising fifth and sixth surfaces; and
   a dielectric layer disposed between the first and second conductive layers and comprising seventh and eighth surfaces,
   wherein the fifth surface of the second conductive layer is directly in contact with the second surface of the substrate, the sixth surface of the second conductive layer is directly in contact with the seventh surface of the dielectric layer, and the eight surface of the dielectric layer is directly in contact with the third surface of the first conductive layer;
   wherein the at least one groove defines a ring in the first conductive layer, and the aperture has a circular shape;
   wherein the at least one groove extends entirely through the dielectric layer and through the first and second conductive layers such that a portion of the second surface of the substrate is exposed, and wherein the aperture extends entirely through the first conductive layer such that a portion of the eighth surface is exposed.

6. The vertical plasmonic interferometer sensor of claim 5, wherein the dielectric layer defines a second optical branch along which surface plasmon polariton modes are excited in response to at least partially coherent light being received by the vertical plasmonic interferometer.

7. The vertical plasmonic interferometer sensor of claim 6, wherein the first optical branch forms a sensing arm of the vertical plasmonic interferometer, and the second optical forms a reference arm of the vertical plasmonic interferometer.

8. The vertical plasmonic interferometer sensor of claim 5, wherein the at least one groove includes a plurality of concentric grooves each being concentric with the aperture.

* * * * *